United States Patent [19]

Henderson

[11] Patent Number: 5,123,438
[45] Date of Patent: Jun. 23, 1992

[54] FLOW CONTROL AND DILUTER SYSTEM FOR BIOASSAY TESTING

[75] Inventor: Robert S. Henderson, Kailua, Hi.

[73] Assignee: The United States of America as represented by the Secretary of the Navy, Washington, D.C.

[21] Appl. No.: 797,505

[22] Filed: Nov. 20, 1991

[51] Int. Cl.$^5$ .............................................. G01N 1/10
[52] U.S. Cl. ............................... 137/255; 137/624.18; 422/100; 436/179
[58] Field of Search ............... 137/255, 263, 571, 572, 137/624.13, 624.18; 422/100, 99; 436/179

[56] References Cited

U.S. PATENT DOCUMENTS

| | | | |
|---|---|---|---|
| 3,891,123 | 6/1975 | Blackburn | 137/255 X |
| 3,930,798 | 1/1976 | Schierjott | |
| 3,994,687 | 11/1976 | Engelbrecht | |
| 4,267,056 | 5/1981 | McClure | |
| 4,564,453 | 1/1986 | Coplot | |
| 4,748,127 | 5/1988 | Siepmann | |
| 4,794,806 | 1/1989 | Nicoli | |
| 4,857,198 | 8/1989 | Meidl | |
| 4,868,129 | 9/1989 | Gibbons | |

*Primary Examiner*—Alan Cohan
*Attorney, Agent, or Firm*—Harvey Fendelman; Thomas Glenn Keough

[57] ABSTRACT

An apparatus is provided for producing specific concentrations of waterborne pollutants diluted in unfiltered seawater and for periodically delivering the seawater/pollutant dilutions to a plurality of experimental test aquaria at selected flow rates. A seawater feed tank containing the unfiltered seawater drains, under the force of gravity, into a seawater feed trough. The seawater feed trough is constructed to allow the unfiltered seawater to escape therefrom at a plurality of seawater escape locations under the force of gravity. A plurality of seawater cells are aligned beneath the seawater feed trough to receive the unfiltered seawater escaping therefrom. Means are further provided to limit the amount of unfiltered seawater in each of the seawater cells to a preselected amount. In a similar fashion, a pollutant feed tank containing the waterborne pollutants drains under the force of gravity into a pollutant feed trough. The pollutant feed trough is constructed to allow the waterborne pollutants to escape therefrom at a plurality of pollutant escape locations under the force of gravity. A plurality of pollutant cells are aligned beneath the pollutant feed trough to receive the waterborne pollutants escaping therefrom. Means are further provided to limit the amount of waterborne pollutants in each of the pollutant cells to a preselected amount. The seawater and pollutant cells are periodically and simultaneously drained under the force of gravity into a plurality of mixing chambers. Each mixing chamber receives the unfiltered seawater drained from one of the seawater cells and pollutants drained from one of the pollutant cells. The resulting seawater/pollutant dilution formed in each of the mixing chambers is then delivered under the force of gravity to one of the experimental test aquaria.

14 Claims, 3 Drawing Sheets

FLOW CONTROL AND DILUTER SYSTEM FOR BIOASSAY TESTING

STATEMENT OF GOVERNMENT INTEREST

The invention described herein may be manufactured and used by or for the Government of the United States for governmental purposes without the payment of any royalties thereon or therefor.

FIELD OF THE INVENTION

The present invention relates to the field of bioassay testing, and more particularly to a flow control and diluter system for providing a controlled flow of seawater/pollutant dilutions to a plurality of experimental test aquaria at selected constant flow rates.

BACKGROUND OF THE INVENTION

In this age of environmental awareness, it has become increasingly more important to study the chronic effects of a variety of pollutants and concentrations thereof on resident marine organisms, especially in pollutant-impacted harbor environs. Simulation of chronic effects are best achieved by flow-through bioassay testing procedures. Simply defined, these procedures provide for a long term (several months) constant flow of pollutants in a controlled marine environment. Typically, outdoor aquaria (or microcosms as they are known) of about 30 to 100 gallon volume are used to simulate the marine ecosystems because of their ability to maintain low to medium diversity assemblage of aquatic organisms for periods of several months.

The microcosms are provided with continuous flow-through of unfiltered seawater and are exposed to normal sunlight. As such, they are linked energetically to the natural world, receiving input of ambient sunlight and nutrients, and can be colonized by larval organisms present in the supply water. In microcosms, many organisms can subsist on available natural foods and can experience near-natural seral development and growth. It is being increasingly recognized that chronic studies performed under such conditions provide a more realistic test of overall toxicity and bioaccumulation of pollutants than tests performed in static setting. Furthermore, extreme variability of concentrations of dissolved toxins, commonly experienced in static tests due to intank degradation and absorption of toxin, is large avoided by continuous addition of toxin to water of flowthrough tests.

Conventional valved systems are unreliable for long-term, precise flow control of unfiltered seawater supplies because valve orifices are easily obstructed by biofouling and other debris. Where seawater is being pumped from high fouling/high sediment environments, valves and piping must be cleaned at least daily to avoid flow alterations. Bioassay diluters of the Mount-Warner-Brungs type, which use automatic siphon tubes and narrow venturi tubes for water delivery and dilution, are suitable only for controlling low flows of filtered water. Some bioassay diluter systems utilize metering devices such as syringe pumps and peristaltic pumps to add toxicant solutions to supply waters of individual tanks. Such systems are prone to frequent malfunction and must be closely monitored for wear of materials such as syringe o-rings and peristaltic tubing. Alternatively, high precision pumps may be employed to maintain a constant flow rate. However, these pumps are expensive and are costly to maintain in high sediment/fouling environments. Furthermore, most bioassay testing operations utilize a plurality of test aquaria thereby requiring several pumps. Thus, a need exists for a flowthrough apparatus that can provide a constant flow of ambient or pollutant-tainted waters to test aquaria without relying on valves or expensive pumps as a primary means of flow rate control.

Therefore, an object of the present invention is to provide a flow control and diluter system that can be used in bioassay testing. Another object of the present invention is to provide a flow-control and diluter system capable of delivering a controlled flow of seawater/pollutant dilutions to a plurality of experimental test aquaria at selected constant flow rates. A further object of the present invention is to provide a flow control and diluter system capable of delivering a controlled flow of seawater/pollutant dilutions over long periods of time while being free of system fouling concerns. Yet another object of the present invention is to provide a flow control and diluter system capable of delivering a controlled flow of seawater/pollutant dilutions even when the seawater generates high levels of biological and/or sediment fouling in the bioassay system. Still another object of the present invention is to provide a flow control and diluter system that is adaptable to a portable design.

SUMMARY OF THE INVENTION

In accordance with the present invention, a portable system is provided for producing specific concentrations of a pollutant mixture diluted in unfiltered seawater and for delivering the seawater/pollutant dilutions to a plurality of experimental test aquaria at selected constant flow rates. A gravity supply tank contains unfiltered seawater from a nearby primary water source. A seawater feed tank receives a constant, gravity fed flow of unfiltered seawater from the gravity supply tank. The seawater feed tank is further provided with means to limit the amount of unfiltered seawater contained therein to a preselected amount. A pollutant mix tank receives a constant, gravity fed flow of unfiltered seawater from the gravity supply tank and a constant flow of pure pollutants from a pollutant supply means containing pure pollutants. The unfiltered seawater and pure pollutants combine to form the pollutant mixture. The pollutant feed tank is further provided with means to limit the amount of pollutant mixture contained therein to a preselected amount. A pollutant feed tank receives a constant, gravity fed flow of the pollutant mixture from the pollutant mix tank. The pollutant feed tank is further provided with means to limit the amount of pollutant mixture contained therein to a preselected amount. A seawater feed trough receives a periodic and predetermined flow of unfiltered seawater from the seawater feed tank under the force of gravity such that the unfiltered seawater is allowed to escape from the seawater feed trough under the force of gravity. Similarly, a pollutant feed trough receives a periodic and predetermined flow of pollutant mixture from the pollutant feed tank under the force of gravity such that the pollutant mixture is allowed to escape from the pollutant feed trough under the force of gravity. A plurality of seawater dose cells are aligned beneath the seawater feed trough to receive the unfiltered seawater escaping from the seawater feed trough. Each of the seawater dose cells is provided with means to limit the amount of unfiltered seawater contained therein to a preselected amount. Similarly, a plurality of pollutant dose cells are aligned beneath the pollutant feed trough to receive the pollutant mixture escaping from the pollutant feed trough. Each of the pollutant dose cells is provided with means to limit the amount of pollutant mixture contained therein to a preselected amount. A plurality of mixing chambers are provided such that each mixing chamber periodically receives a gravity fed flow of the preselected amount of unfiltered seawater and the preselected amount of pollutant mixture under the force of gravity from a particular seawater dose cell/pollutant dose cell pair. The aforementioned seawater/pollutant dilution is formed within each of the mixing chambers and is delivered under the force of gravity to one of the experimental test aquaria.

DESCRIPTION OF THE PREFERRED EMBODIMENT

Figure 1:
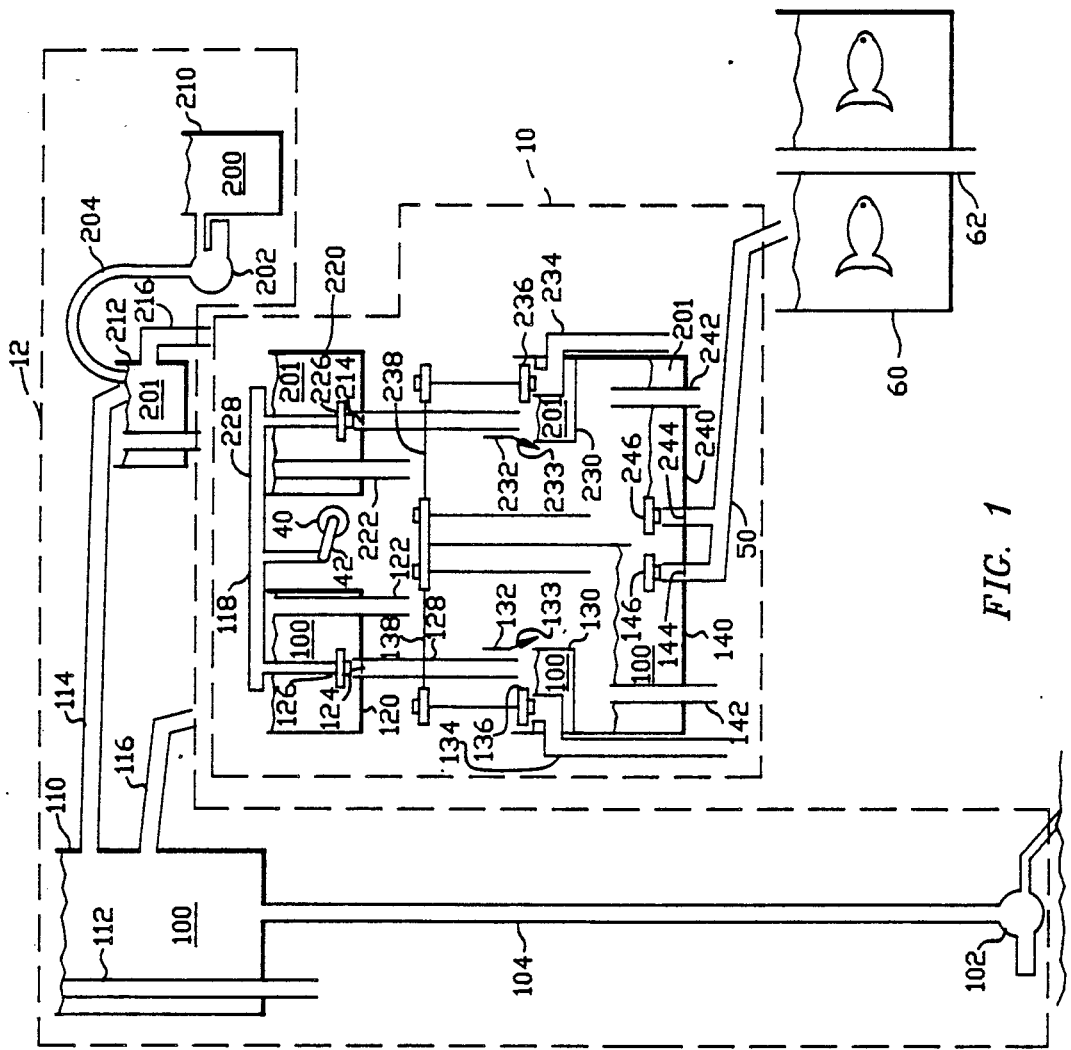
FIG. 1 is a schematic representation of the primary components of the flow control and diluter system according to the present invention.

Referring now to the drawings, and in particular to FIG. 1, a schematic representation depicting the primary components of the flow control and diluter system according to the present invention can be found within the dotted line box referenced by the numeral 10. It is to be understood at the outset that this is a representative embodiment employing the inventive concepts of the present invention. As such, it will be readily apparent to one skilled in the art that the present invention could be practiced other than as shown without departing from the novel features explained further hereinbelow. Further, the operation of system 10 will be described as it functions with its upstream components found within the dotted line box referenced by the numeral 12. Incorporation of upstream components 12 allows the present invention to exist as a self-contained system. Accordingly, the present invention built with upstream components 12 lends itself to a portable design.

In FIG. 1, ambient or unfiltered seawater 100 from a nearby water source is delivered by a pump 102 via conduit 104 to a gravity supply tank 110. (Note that any untainted seawater contained within upstream components 12 or system 10 is referenced by numeral 100. In addition, for ease of understanding, any element/component of the present invention that is associated with untainted seawater will be referenced by a numeral in the 100's.) Gravity supply tank 110 is typically situated on a tower (not shown) such that its bottom is located at a higher elevation than the highest level of seawater 100 in system 10. This insures that there is a sufficient amount of pressure to supply seawater to system 10. Gravity supply tank 110 is also typically configured with an overflow standpipe 112 to prevent any overflow of seawater onto or into the components in system 10. Standpipe 112 could be configured to drain to some common drain (not shown).

A supply of pure pollutants 200, contained within a reservoir 210, is constantly pumped by a metering pump 202 via conduit 204 into a pollutant mix tank 212. At the same time, seawater from gravity supply tank 110 is allowed to flow under the force of gravity into pollutant mix tank 212 via conduit 114. In this way, a specific concentration, waterborne pollutant mixture 201 is formed. (Note that any pollutant mixture contained within upstream components 12 or system 10 is referenced by the numeral 201. In addition, for ease of understanding, any element/component of the present invention that is associated with the pollutant mixture from pollutant mix tank 212 will be referenced by a numeral in the 200's.) The specific concentration of pollutant mixture 201 is held constant by providing a constant flow of seawater 100 and pure pollutants 200. Finally, an overflow standpipe 214 is typically provided to drain to the aforementioned common drain to prevent the overflow of any pollutant mixture 201 onto or into system 10. As with gravity supply tank 110, pollutant mix tank 212 must be located at a height greater than that of pollutant mixture 201 in system 10. Seawater 100 and pollutant mixture 201 are allowed to feed under the force of gravity through conduits 116 and 216, respectively, into system 10. The flow of seawater 100 through the various "seawater" components of system 10 will now be described. Since the flow of pollutant mixture 201 mirrors that of seawater 100, the description to follow is also applicable to the flow of pollutant mixture 201 through its various "pollutant" components. Accordingly, the description of the identical portions of system flow will be limited to that of seawater 100. (Note that the mirror image "pollutant" components have been assigned corresponding reference numerals in the 200's.)

A seawater feed tank 120 receives a constant, gravity fed flow of seawater 100 via conduit 116. An overflow standpipe 122, draining to the common drain, is provided to limit the volume of seawater contained therein to a preselected level. A drainage port 124 located in the bottom of tank 120 is sealed by a cap valve 126. The details, operation and function of cap valve 126 will be explained further herein below. Essentially, when cap valve 126 is sealed, tank 120 fills to the preselected amount governed by standpipe 122. When cap valve 126 is opened, the preselected amount of seawater is allowed to drain under the force of gravity trough drainage port 124.

Practically speaking, most bioassay testing applications must be designed to supply a flow of pollutant-tainted water to a plurality of test aquaria. Thus, it is desirable to provide a system that can accommodate the plurality of test aquaria with a minimum of pumps, valves, etc. Accordingly, gravity fed seawater draining through drainage port 124 flows through conduit 128 and into a seawater feed through 130. Trough 130 is designed to allow the received seawater to escape therefrom under the force of gravity into a plurality of seawater dose cells, only one of which is shown in FIG. 1 and referenced by numeral 140. The "plurality" capability of the present invention will be explained further hereinbelow.

Escape of seawater 100 from trough 130, as indicated by flow arrow 133, is provided for by slots, one of which is shown in FIG. 1 and referenced by numeral 132. Slot 132 is aligned over a respective seawater dose cell 140. By placing a slot 132 over each seawater dose cell 140, each cell 140 is allowed to fill to a level dictated by the height of overflow standpipe 142.

Also provided within seawater feed trough 130 is drain/bypass pipe 134 and corresponding cap valve 136. Bypass 134 is configured such that, when cap valve 136 is opened, seawater 100 within trough 130 is drained to a level below that of slot 132 thereby inhibiting the escape of seawater from trough 130. Although illustrated as a single pipe and valve in FIG. 1, it is within the scope of the present invention that bypass 134 and cap valve 136 could be multiple pipes and valves if desirable to facilitate expeditious drainage. Details of the operation and function of cap valve 136 will follow hereinbelow.

As mentioned above, each seawater dose cell 140 fills to a level dictated by the height of overflow standpipe 142. A drainage port 144 is located in the bottom of cell 140 and is sealed by a cap valve 146. Once again, the detailed operation and function of cap valve 146 will follow hereinbelow. Essentially, when cap valve 146 is sealed, cell 140 fills to its preselected level. When cap valve 146 is opened, the preselected amount of seawater is allowed to drain under the force of gravity through drainage port 144.

The gravity fed seawater draining through drainage port 144 flows into a mixing chamber 50. At the same time, a cap valve 246 is opened in a corresponding pollutant dose cell 240 to allow the pollutant mixture 201 to flow under the force of gravity into mixing chamber 50. Accordingly, while only one is shown in FIG. 1, a plurality of mixing chambers 50 are provided such that one mixing chamber is available for each seawater/pollutant dose cell pair. Since the amounts of seawater 100 and pollutant mixture 201 are fixed by standpipes 142 and 242, respectively, the concentration of the seawater/pollutant dilution is held constant each time cap valves 146 and 246 are opened. Each mixing chamber 50 is then allowed to drain under the force of gravity into a selected test aquaria 60 housing the living organisms (i.e., fish, plants, etc.) under examination. Typically, an overflow standpipe 62 is maintained in test aquaria 60 in order to prevent overflow.

Control of the plurality of cap valves utilized by system 10 will now be described with the aid of FIGS. 1, 2 and 3 where like reference numerals have been used for common elements. The periodic operations and function of the cap valves will first be described with reference again to FIG. 1 and a representative structure of accomplishing same will then be described with reference to FIGS. 2 and 3. A drive shaft 30 connected to a variable speed motor (not shown in FIG. 1) rotates a cam 32 attached to drive shaft 30. Each rotation of cam 32 depresses a microswitch (not shown in FIG. 1 for purposes of clarity) which, while being depressed, activates electro-mechanical actuator 40. Actuator 40 electrically operates a mechanical lever 42 which is mechanically connected to cap valves 126 and 226 by a combination of connecting rods and shafts designated by reference numerals 128 and 228, respectively. Connection of actuator 40, as well as the means for mechanically connecting same to cap valves 126 and 226, may be accomplished by means that are well known in the art. During the time that cap valves 126 and 226 are opened, the seawater 100 and pollutant mixture 201 drain from tanks 120 and 220, respectively. Thus, the variable speed motor is adjusted such that the microswitch is depressed long enough to allow the filled tanks to empty into troughs 130 and 230. When cam 32 rotates away from the microswitch, cap valves 126 and 226 are closed so that tanks 120 and 220 may refill. This cycle is repeated for each rotation of drive shaft 130.

A second cam (not shown in FIG. 1 for purposes of clarity) is mounted on drive shaft 30. This second cam is configured such that, during each rotation of drive shaft 30, the cam mechanically opens and closes cap valves 136, 236, 146 and 246 by a combination of connecting rods and shafts 138, 238, 148 and 248, respectively. The second cam is further configured to open these cap valves only when cap valves 126 and 226 are closed. In addition, as will be explained hereinbelow with reference to FIG. 3, the second cam is configured to open cap valves 136 and 236 prior to opening cap valves 146 and 246. In this way, the levels of seawater and pollutant mixture in troughs 130 and 230, respectively, are lowered below the level of slots 132 and 232 before the seawater and pollutant mixture are released into the mixing chambers. Thus, the amount of seawater and pollutant mixture exiting a seawater/pollutant dose cell pair is limited to the preselected amounts fixed by standpipes 142 and 242.

Figure 2:
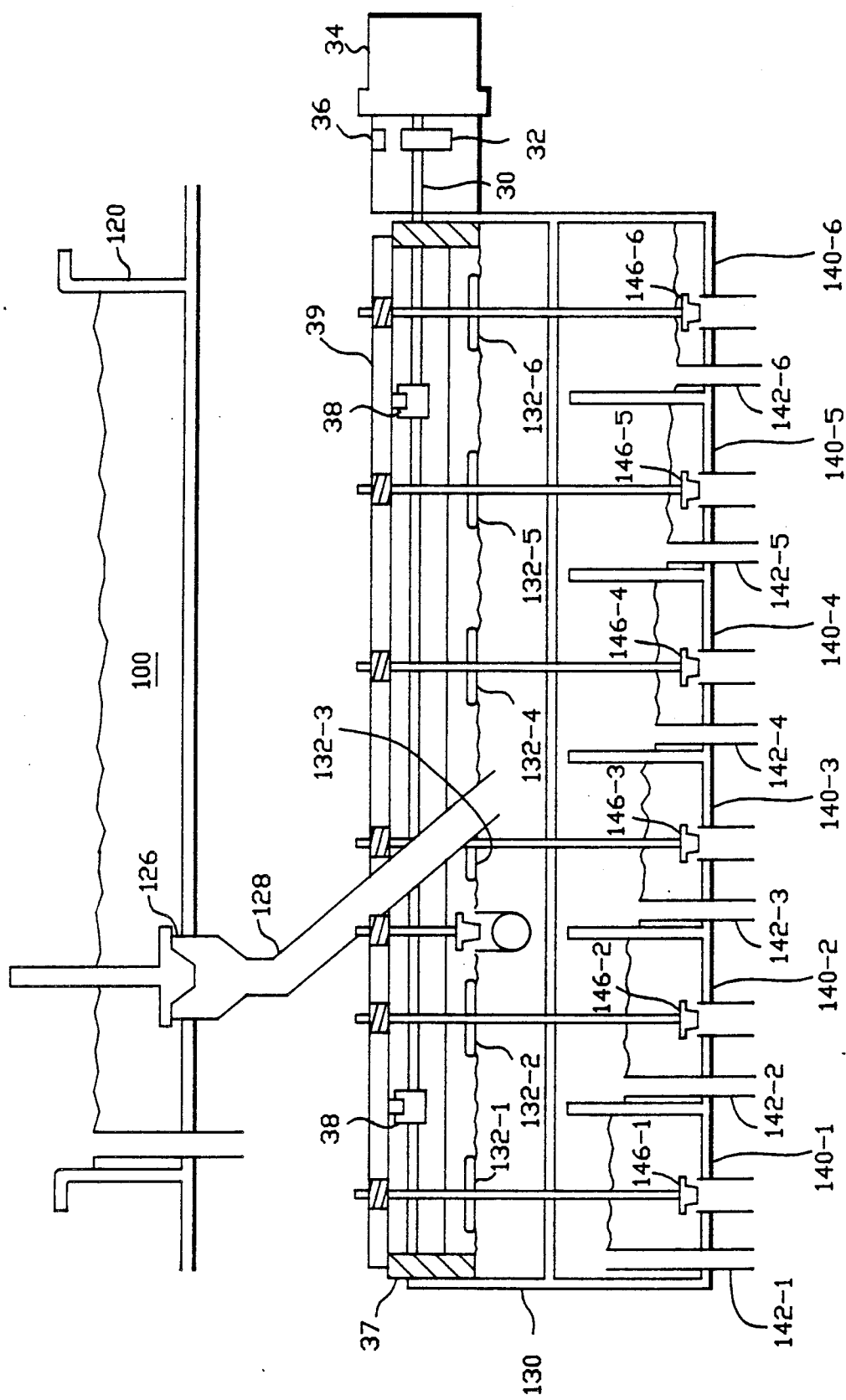
FIG. 2 is a side, cross-sectional view of the flow control and diluter system of the present invention.

Referring now to FIG. 2, a side, cross-sectional view of system 10 is shown for the "seawater side" of system 10. It is to be appreciated that a mirror image "pollutant side" of system 10 exists and functions identically as the shown "seawater side". Accordingly, only the "seawater" side will be explained further hereinbelow. As is readily apparent, seawater feed tank 120 feeds seawater feed trough 130 under the force of gravity by means of conduit 128. The seawater feed trough 130 is positioned above the seawater dose cells 140. For purposes of description, six seawater dose cells 140—1,—, 140—6 are shown although the present invention may be practiced with as few or as many seawater dose cells as required. Similarly, slots 132—1,—, 132—6 are positioned above their respective dose cell to allow seawater to escape therethrough. Associated standpipes, drainage ports and cap valves are provided in each seawater dose cell and are referenced accordingly. Once again, note that the levels contained in each dose cell can be adjusted by the height of its respective overflow standpipe.

Drive shaft 30 is shown having cam 32 attached thereto such that each rotation of same by variable speed motor 34 will cause microswitch 36 to be depressed. As mentioned above, depression of microswitch 36 will allow cap valves 126 and 226 to open. Drive shaft 30 further extends over the length of system 10 and is positioned by guide blocks 37 at either end of system 10. The second cam 38 affixed to rotate with drive shaft 30 is positioned to raise and lower a valve lift bar 39 only when cap valve 126 is closed as shown. Typically, more than one cam 38 may be required for load bearing purposes to raise and lower valve lift bar 39. Accordingly, two are shown in FIG. 2.

Figure 3:
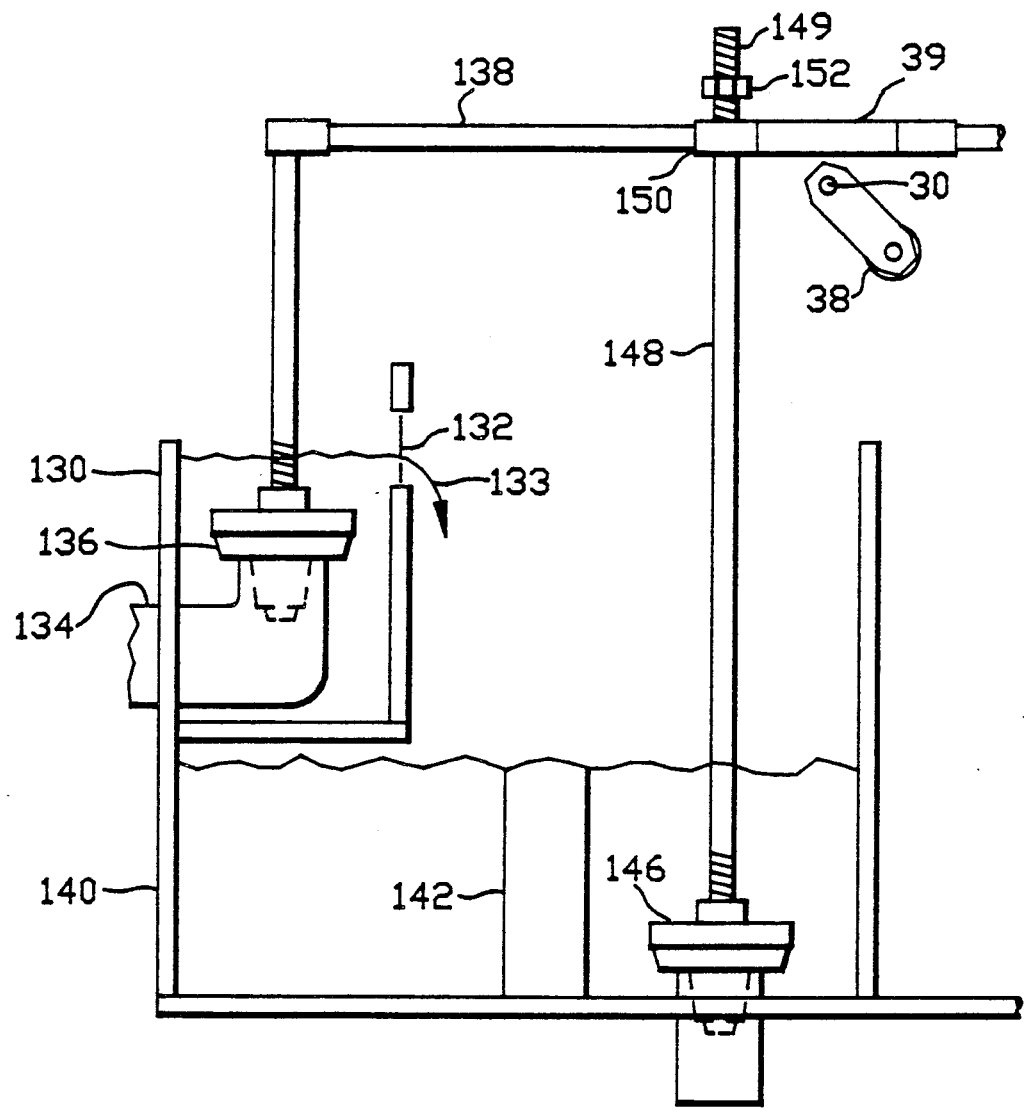
FIG. 3 is an enlarged end view of the seawater feed trough, a seawater dose cell and their associated combination of cap valves and connecting rods and shafts.

Referring now to FIG. 3, an enlarged end view of seawater feed trough 130 and a seawater dose cell 140 is shown along with its associated combination of connecting rods and shafts 138 and 148. Once again, common reference numerals are used where appropriate. It is to be understood that this configuration is just one representative embodiment and that other means of achieving this operation are well known in the art. In particular, second cam 38 may be a wheel cam configured to raise connecting rod and shaft 138 as Cam 38 rotates with drive shaft 30 and contacts Valve lift bar 39. In order to open cap valve 136 prior to opening cap valve 146, cap valve 136 is raised in a direct relationship with valve bar 39. In this way, the seawater in trough 130 is allowed to drain by gravity through bypass pipe 134 to a level below the escape slot 132. This prevents any additional seawater from escaping into seawater dose cell 140 when cap valve 146 is eventually opened.

In order to delay the opening of cap valve 146, connecting shaft 148 passes freely through a guide block 150 that is fixed in relation to connecting rod and shaft combination 138. Connecting shaft 148 terminates in a threaded end 149. An adjusting nut 152 is placed on threaded end 149. Nut 152 is adjusted such that guide block 150 raises up against nut 152 to open cap valve 146 only after the seawater level in trough 130 drops below the level of slot 132. As cam 38 rotates away from lifting bar 39, cap valve 136 (as well as cap valves 236, 146 and 246) close. The above described cycle is repeated for each revolution of drive shaft 30. To further increase the adjustable nature of the present invention, threaded ends and corresponding adjusting nuts may also be provided where each cap valve is connected to its rod and shaft combination.

The advantages of the present invention are numerous. The flow control and diluter system of the present invention provides a novel means for producing specific concentrations of a pollutant mixture diluted in seawater and for delivering the resultant dilutions to a plurality of test aquaria. Production and delivery to the plurality of seawater/pollutant dilutions is achieved without the need for high precision pumps. Indeed, only two pumps are possibly needed to supply the seawater and pollutant to a plurality of test aquaria. In addition, by relying on simply operated, relatively large orifice cap valves, the possibility of clogging within the system is minimized. For most bioassay applications, the various conduits, standpipes and drainage ports used in the present invention would have minimum inside diameters of one-half inch, and more typically would have inside diameters ranging from one to two inches. The novel arrangement of feed tanks, troughs, dose cells and simple means for controlling gravity fed flow therebetween, allow the present invention to be assembled for a fraction of the cost of the aforementioned high precision pumps. Furthermore, system maintenance is greatly reduced since areas subject to clogging or fouling are greatly reduced.

Although the invention has been described relative to a specific embodiment thereof, there are numerous variations and modifications that will be readily apparent to those skilled in the art in the light of the above teachings. For example, the size of the tanks, conduits, drainage ports, standpipes and slots are design considerations based upon factors such as desired flow rates, the amount of sediment and fouling potential in the seawater and the viscosity of the pollutant mixture, just to name a few. Similarly, the choice of material used to construct the components of the present invention may be varied. Typically, PVC and nylon materials could be used since they are corrosion resistant. It is therefore to be understood that, within the scope of the appended claims, the invention may be practiced other than as specifically described.

What is claimed as new and desired to be secured by Letters Patent of the United States is:

1. An apparatus for producing specific concentrations of waterborne pollutants diluted in unfiltered seawater and for periodically delivering the seawater/pollutant dilutions to a plurality of experimental test aquaria at selected flow rates, comprising:

a seawater feed tank containing the unfiltered seawater, said seawater feed tank further having means to selectively drain the unfiltered seawater therefrom under the force of gravity;

a seawater feed trough for receiving the unfiltered seawater drained from said seawater feed tank, said seawater feed trough further having means for allowing the unfiltered seawater to escape therefrom at a plurality of seawater escape locations under the force of gravity;

a plurality of seawater cells for receiving the unfiltered seawater escaping from said seawater feed trough, each of said seawater cells being positioned to receive the unfiltered seawater from a corresponding one of the plurality of seawater escape locations;

means for limiting the amount of unfiltered seawater in each of said seawater cells to a preselected amount;

a pollutant feed tank containing the waterborne pollutants, said pollutant feed tank further having means to selectively drain the waterborne pollutants therefrom under the force of gravity;

a pollutant feed trough for receiving the waterborne pollutants drained from said pollutant feed tank, said pollutant feed trough further having means for allowing the waterborne pollutants to escape therefrom at a plurality of pollutant escape locations under the force of gravity;

a plurality of pollutant cells for receiving the waterborne pollutants escaping from said pollutant feed trough, each of said pollutant cells being positioned to receive the waterborne pollutants from a corresponding one of the plurality of pollutant escape locations;

means for limiting the amount of waterborne pollutants in each of said pollutant cells to a preselected amount;

means for periodically and simultaneously draining said seawater and pollutant cells of the preselected amount of unfiltered seawater and waterborne pollutants, respectively, under the force of gravity; and a plurality of mixing chambers, each of said mixing chambers receiving the unfiltered seawater drained from one of said seawater cells and pollutants drained from one of said pollutant cells, wherein the seawater/pollutant dilution is formed in each of said mixing chambers and delivered under the force of gravity to one of the experimental test aquaria.

2. An apparatus as in claim 1 wherein said limiting means in each of said seawater and pollutant cells is an adjustable height, overflow standpipe configured to drain off excess unfiltered seawater or waterborne pollutants, respectively, under the force of gravity.

3. An apparatus as in claim 1 further comprising means for preventing the escape of unfiltered seawater and waterborne pollutants from said seawater feed trough and said pollutant feed trough, respectively, when said seawater and pollutant cells are periodically and simultaneously drained.

4. An apparatus for producing specific concentrations of waterborne pollutants diluted in unfiltered seawater and for periodically delivering the seawater/pollutant dilutions to a plurality of experimental test aquaria at selected flow rates, comprising:

a seawater feed tank containing the unfiltered seawater, said seawater feed tank further having a gravity fed drainage port sealed by a cap valve, wherein said seawater feed tank cap valve is periodically raised from its drainage port to allow the unfiltered seawater to drain therefrom;

a seawater feed trough for receiving the unfiltered seawater drained from said seawater feed tank, said seawater feed trough further having means for allowing the unfiltered seawater to escape therefrom at a plurality of seawater escape locations under the force of gravity;

a plurality of seawater cells for receiving the unfiltered seawater escaping from said seawater feed trough, each of said seawater cells being positioned to receive the unfiltered seawater from a corresponding one of the plurality of seawater escape locations, each of said seawater cells further having a gravity fed drainage port sealed by a cap valve;

means for limiting the amount of unfiltered seawater in each of said seawater cells to a preselected amount;

a pollutant feed tank containing the waterborne pollutants, said pollutant feed tank further having a gravity fed drainage port sealed by a cap valve, wherein said pollutant feed tank cap valve is periodically raised from its drainage port to allow the waterborne pollutants to drain therefrom;

a pollutant feed trough for receiving the waterborne pollutants drained from said pollutant feed tank, said pollutant feed trough further having means for allowing the waterborne pollutants to escape therefrom at a plurality of pollutant escape locations under the force of gravity;

a plurality of pollutant cells for receiving the waterborne pollutants escaping from said pollutant feed trough, each of said pollutant cells being positioned to receive the waterborne pollutants from a corresponding one of the plurality of pollutant escape locations, each of said pollutant cells further having a gravity fed drainage port sealed by a cap valve;

means for limiting the amount of waterborne pollutants in each of said pollutant cells to a preselected amount;

means for periodically and simultaneously raising said seawater cell cap valves and said pollutant cell cap valves to drain said seawater and pollutant cells, respectively, under the force of gravity; and a plurality of mixing chambers, each of said mixing chambers receiving the unfiltered seawater drained from one of said seawater cells and pollutants drained from one of said pollutant cells, wherein the seawater/pollutant dilution is formed in each of said mixing chambers and delivered under the force of gravity to one of the experimental test aquaria.

5. An apparatus as in claim 4 wherein said limiting means in each of said seawater and pollutant cells is an adjustable height, overflow standpipe configured to drain off excess unfiltered seawater or waterborne pollutants, respectively, under the force of gravity.

6. An apparatus as in claim 4 further comprising means for preventing the escape of unfiltered seawater and waterborne pollutants from said seawater feed trough and said pollutant feed trough, respectively, when said seawater and pollutant cells are periodically and simultaneously drained.

7. An apparatus as in claim 6 wherein said preventing means in each of said seawater feed trough and said pollutant feed trough comprises a gravity fed drainage port sealed by a cap valve, wherein said seawater feed trough cap valve and said pollutant feed trough cap valve are periodically raised from their respective drainage ports to allow the unfiltered seawater and waterborne pollutants, respectively, to drain therefrom to a level below the seawater and pollutant escape locations at a time prior to the periodic and simultaneous draining of said seawater and pollutant cells.

8. An apparatus as in claim 4 further comprising:

a variable speed motor having a rotating shaft;

first cam means fixed to the shaft of said motor to rotate with same;

switch means in communication with said first cam means on each rotation of the shaft of said motor; and an electro-mechanical actuator electrically connected to said switch means and mechanically connected to said seawater tank cap valve and said pollutant feed tank cap valve, wherein each communication of said first cam means with said switch means activates said electro-mechanical actuator to raise said seawater feed tank cap valve and said pollutant feed tank cap valve.

9. An apparatus as in claim 8 wherein said plurality of seawater cells are aligned in a first row and said plurality of pollutant cells are aligned in a second row adjacent to said first row, said apparatus further comprising:

second cam means fixed to the shaft of said motor to rotate with same;

a valve lift bar extending the length of said first and second rows and in communication with said second cam means on each rotation of the shaft of said motor; and means connecting each of said seawater cell cap valves and each of said pollutant cell cap valves to said valve lift bar, wherein each communication of said second cam means with said valve lift bar raises said lift bar thereby raising each of said seawater cell cap valves and said pollutant cell cap valves.

10. An apparatus as in claim 7 wherein said plurality of seawater cells are aligned in a first row and said plurality of pollutant cells are aligned in a second row adjacent to said first row, said apparatus further comprising:

a variable speed motor having a rotating shaft;

first cam means fixed to the shaft of said motor to rotate with same;

switch means in communication with said first cam means on each rotation of the shaft of said motor;

an electro-mechanical actuator electrically connected to said switch means and mechanically connected to said seawater tank cap valve and said pollutant feed tank cap valve, wherein each communication of said first cam means with said switch means activates said electro-mechanical actuator to raise said seawater feed tank cap valve and said pollutant feed tank cap valve;

second cam means fixed to the shaft of said motor to rotate with same;

a valve lift bar extending the length of said first and second rows and in communication with said second cam means on each rotation of the shaft of said motor;

means connecting said seawater feed trough cap valve and said pollutant feed trough cap valve to said valve lift bar; and means connecting each of said seawater cell cap valves and each of said pollutant cell cap valves to said valve lift bar, wherein each communication of said second cam means with said valve lift bar raises said lift bar to first raise said seawater feed trough cap valve and said pollutant feed trough cap valve and subsequently raise each of said seawater cell cap valves and said pollutant cell cap valves.

11. A system for producing specific concentrations of a pollutant mixture diluted in unfiltered seawater and for periodically delivering the seawater/pollutant dilutions to a plurality of experimental test aquaria at selected flow rates, comprising:

a gravity supply tank containing the unfiltered seawater from a nearby primary water source;

a seawater feed tank for receiving a constant, gravity fed flow of unfiltered seawater from said gravity supply tank, said seawater feed tank being further provided with means to limit the amount of unfiltered seawater contained therein to a preselected amount;

pollutant supply means containing pure pollutants;

a pollutant mix tank for receiving a constant, gravity fed flow of unfiltered seawater from said gravity supply tank and a constant flow of pure pollutants from said pollutant supply means whereby the unfiltered seawater and pure pollutants combine to form the pollutant mixture, said pollutant mix tank being further provided with means to limit the amount of pollutant mixture contained therein to a preselected amount;

a pollutant feed tank for receiving a constant, gravity fed flow of the pollutant mixture from said pollutant mix tank, said pollutant feed tank being further provided with means to limit the amount of pollutant mixture contained therein to a preselected amount;

a seawater feed trough for receiving a periodic and predetermined flow of unfiltered seawater from said seawater feed tank under the force of gravity, wherein the unfiltered seawater is allowed to escape from said seawater feed trough under the force of gravity;

a pollutant feed trough for receiving a periodic and predetermined flow of pollutant mixture from said pollutant feed tank under the force of gravity, wherein the pollutant mixture is allowed to escape from said pollutant feed trough under the force of gravity;

a plurality of seawater dose cells aligned beneath said seawater feed trough for receiving the unfiltered seawater escaping from said seawater feed trough, each of said seawater dose cells being provided with means to limit the amount of unfiltered seawater contained therein to a preselected amount;

a plurality of pollutant dose cells aligned beneath said pollutant feed trough for receiving the pollutant mixture escaping from said pollutant feed trough, each of said pollutant dose cells being provided with means to limit the amount of pollutant mixture contained therein to a preselected amount; and a plurality of mixing chambers, each of said mixing chambers periodically receiving a gravity fed flow of the preselected amount of unfiltered seawater and the preselected amount of pollutant mixture under the force of gravity from a particular seawater dose cell/pollutant dose cell pair, wherein the seawater/pollutant dilution is formed within each of said mixing chambers and is delivered under the force of gravity to one of the experimental test aquaria.

12. A system as in claim 11 further comprising means for pumping the unfiltered seawater from the primary water source into said gravity supply tank.

13. A system as in claim 11 further comprising means for controlling the periodic and predetermined flow of unfiltered seawater and pollutant mixture from said seawater and pollutant feed tanks, respectively, and for controlling the periodic flow of the preselected amounts of unfiltered seawater and pollutant mixtures from said plurality of seawater and pollutant dose cells, respectively, wherein flow from said plurality of seawater and pollutant dose cells is inhibited during the periodic flow from said seawater and pollutant feed tanks, and wherein flow from said seawater and pollutant feed tanks is inhibited during the periodic flow from said plurality of seawater and pollutant dose cells.

14. A system as in claim 13 wherein said means for controlling further comprises means for inhibiting receipt, by said plurality of seawater and pollutant dose cells, of the unfiltered seawater and pollutant mixture from said seawater and pollutant feed troughs, respectively, during the periodic flow from said plurality of seawater and pollutant dose cells.

* * * * *